United States Patent
Haitin et al.

(10) Patent No.: US 6,636,780 B1
(45) Date of Patent: Oct. 21, 2003

(54) MEDICATION DISPENSING SYSTEM INCLUDING MEDICINE CABINET AND TRAY THEREFOR

(75) Inventors: David Haitin, Tel Aviv (IL); Gilead Asseo, Kfar Shmaryahu (IL)

(73) Assignee: MDG Medical Inc., Or Yehuda (IL)

( * ) Notice: Subject to any disclaimer, the term of this patent is extended or adjusted under 35 U.S.C. 154(b) by 179 days.

(21) Appl. No.: 09/706,872

(22) Filed: Nov. 7, 2000

(51) Int. Cl.$^7$ .................. G06F 17/00; G07F 11/00
(52) U.S. Cl. .............. 700/236; 700/242; 700/244; 700/241; 221/2; 221/7
(58) Field of Search ............... 700/241, 242, 700/243, 244, 236, 237; 705/2, 3; 368/1, 11; 221/2, 7

(56) References Cited

U.S. PATENT DOCUMENTS

| | | | |
|---|---|---|---|
| 4,695,954 A | * 9/1987 | Rose et al. ............. 364/413 |
| 4,785,969 A | 11/1988 | McLaughlin | |
| 4,847,764 A | 7/1989 | Halvorson | |
| 4,857,713 A | 8/1989 | Brown | |
| 4,857,716 A | 8/1989 | Gombrich et al. | |
| 4,962,491 A | * 10/1990 | Schaeffer ............. 368/21 |
| 4,967,928 A | * 11/1990 | Carter ............. 221/2 |
| 5,014,875 A | 5/1991 | McLaughlin et al. | |
| 5,314,243 A | 5/1994 | McDonald et al. | |
| 5,335,816 A | * 8/1994 | Kaufman et al. ........... 221/13 |
| 5,346,297 A | * 9/1994 | Colson et al. ............. 312/215 |
| 5,377,864 A | * 1/1995 | Blechl et al. ............. 221/2 |
| 5,431,299 A | * 7/1995 | Brewer et al. ............. 221/2 |
| 5,460,294 A | 10/1995 | Williams | |
| 5,520,450 A | * 5/1996 | Colson et al. ............. 312/215 |
| 5,564,803 A | 10/1996 | McDonald et al. | |
| 5,582,323 A | * 12/1996 | Kurtenbach ............. 221/2 |
| 5,673,983 A | 10/1997 | Carlson et al. | |
| 5,713,485 A | 2/1998 | Liff et al. | |
| RE35,743 E | 3/1998 | Pearson | |
| 5,745,366 A | 4/1998 | Higham et al. | |
| 5,758,095 A | 5/1998 | Albaum et al. | |
| 5,797,515 A | 8/1998 | Liff et al. | |
| 5,842,976 A | 12/1998 | Williamson | |
| 5,845,255 A | 12/1998 | Mayaud | |
| 5,845,264 A | 12/1998 | Nelhaus | |
| 5,880,443 A | * 3/1999 | McDonald et al. ......... 235/375 |
| 5,883,806 A | 3/1999 | Meador et al. | |
| 5,905,653 A | 5/1999 | Higham et al. | |
| 5,912,818 A | 6/1999 | McGrady et al. | |
| 5,927,540 A | 7/1999 | Godlewski | |
| 5,971,594 A | * 10/1999 | Sahai et al. ............. 700/242 |

(List continued on next page.)

FOREIGN PATENT DOCUMENTS

WO  WO 99/43284 A1 * 9/1999 ............. A61J/7/04

Primary Examiner—Donald P. Walsh
Assistant Examiner—Michael E. Butler
(74) Attorney, Agent, or Firm—Evelyn H. McConathy; Dilworth Paxson LLP (57) ABSTRACT

A medication dispensing system includes a medicine cabinet having a plurality of compartments for containing supplies of different kinds of medications to be accessed by a healthcare attendant for preparing individual medication dosages for named patients; and a tray having a plurality of sections for receiving a plurality of receptacles each adapted to contain one or more medication dosages prescribed for a named patient. The medicine cabinet includes a processor having a memory for storing the names of patients and their prescribed medication dosages, and a display screen for displaying the patient names and their respective prescribed medication dosages. The tray includes a display screen for displaying the patient names and their respective medication dosages, and a communication link with the medicine cabinet through which the cabinet processor communicates to the tray the patient names and their respective medication dosages.

21 Claims, 5 Drawing Sheets

U.S. PATENT DOCUMENTS

| | | |
|---|---|---|
| 6,003,006 A | 12/1999 | Colella et al. |
| 6,011,999 A | 1/2000 | Holmes |
| 6,021,392 A | 2/2000 | Lester et al. |
| 6,032,155 A | 2/2000 | de la Huerga |
| 6,068,156 A | 5/2000 | Liff et al. |
| 6,112,502 A | 9/2000 | Frederick et al. |
| 6,138,865 A * | 10/2000 | Gilmore ........................ 221/2 |
| 6,151,536 A * | 11/2000 | Arnold et al. ............... 700/237 |
| 6,152,364 A * | 11/2000 | Schoonen et al. .......... 235/375 |
| 6,170,230 B1 * | 1/2001 | Chudy et al. ................. 53/168 |
| 6,170,929 B1 | 1/2001 | Wilson et al. |
| 6,189,727 B1 * | 2/2001 | Shoenfeld ...................... 221/2 |
| 6,272,394 B1 | 8/2001 | Lipps |
| 6,272,481 B1 | 8/2001 | Lawrence et al. |
| 6,294,999 B1 * | 9/2001 | Yarin et al. ............... 340/573.1 |
| 6,304,797 B1 * | 10/2001 | Shusterman ................. 700/243 |
| 6,347,329 B1 | 2/2002 | Evans |
| 6,352,200 B1 | 3/2002 | Schoonen et al. |
| 6,385,505 B1 | 5/2002 | Lipps |
| 2001/0002448 A1 | 5/2001 | Wilson et al. |
| 2002/0027507 A1 | 3/2002 | Yarin et al. |
| 2002/0032582 A1 | 3/2002 | Feeney, Jr. et al. |
| 2002/0035484 A1 | 3/2002 | McCormick |
| 2002/0070226 A1 | 6/2002 | Liff et al. |
| 2002/0091546 A1 | 7/2002 | Christakis et al. |
| 2002/0095424 A1 | 7/2002 | Chung |

* cited by examiner

MEDICATION DISPENSING SYSTEM INCLUDING MEDICINE CABINET AND TRAY THEREFOR

FIELD AND BACKGROUND OF THE INVENTION

The present invention relates to medication dispensing systems, and also to a novel medicine cabinet structure and a novel tray structure for use in such systems.

Automated medication dispensing systems have been in use for many years. The initial purpose of such systems was to reduce the high rates of medication errors associated with manual distribution. The literature indicates that medication errors occur in the following areas: 55% at ordering, 33% at administration, 6% at transportation and 5% at dispensing. The current automated systems present more sophisticated advantages, including: lower costs associated with pharmaceutical distribution, reduction of personnel, inventory control, substance control, automated documentation, further reduction of errors, and relieving professional pharmacists and nursing personnel of many tasks.

There are two types of dispensing systems currently employed in medical facilities: centralized systems, and decentralized systems.

The centralized systems are based on the transfer of the physician's orders/prescription to the central pharmacy of the medical facility. These systems facilitate the transfer of these orders to the central pharmacy after being reviewed by personnel in the ward/floor, whereupon the orders are reviewed, authorized and filled by a pharmacist, sent as a unit dose to the ward, and then dispensed to the appropriate patient. Centralized systems are used primarily in the U.S.A. They are costly and very inefficient, mainly because of the use of a large trained staff.

Decentralized systems are based on ward stocks managed by trained nursing personnel in conjunction with dedicated pharmacists from the hospital pharmacy to the given department. The dispensing procedure traditionally proceeds as follows:

1. The nurse receives from the physician the prescription/s stating the medication, time of delivery, and route (p.o., i.v., etc.).
2. At the appropriate time, the nurse retrieves the appropriate medication/s for the patients according to a list of orders, places the medications into a receptacle, usually with an attachment that indicates the patient's name, places the receptacles on a tray, and then commences to dispense the receptacles to the patients in the ward.

The foregoing traditional method is subject to a number of disadvantages including: (1) possible confusion between patient files; (2) errors in brand or dosage when retrieving medications from the medicine cabinet; (3) errors in identifying individual patients; (4) errors in receptacle identification; (5) demanding much of the nurse's time; (6) possibility of mistakes in inventory keeping and pharmacy ordering; and (7) very low degree of control even though expensive and narcotic drugs are involved.

A report from the Institute of Medicine (IOM) of the National Academies released in November 1999 in the U.S.A. calls on Congress to create a national patient safety center to develop new tools and systems, the reason being alarming figures regarding human cost of medical errors. Deaths from medical errors are estimated, according to different studies, to be between 44,000 to 98,000 people in the U.S. hospitals each year, more than those from highway accidents, breast cancer or aids. . The report states that illegible handwriting, and the treatment of patients by several practitioners that do not have complete information about the medicines prescribed and the patient's illnesses, are part of the basic flaws in the way the health system is presently organized. William Richardson, chairman of the committee, is quoted saying "It may be part of human nature to err, but it is also part of human nature to create solutions, find better alternatives, and meet the challenges ahead"

Medication management devices generally fall under three categories: (a) automated devices in the central pharmacy area; (b) automated devices in the patient care unit; and (c) point-of-care information systems.

The primary goal of centrally-located devices is to replace or improve the current manual process for filling unit dose carts. These devices offer the advantage of a single, centralized inventory and a lower overall inventory. Disadvantages of such devices include large size, high cost, and reliance on efficient delivery systems from the central pharmacy Patient care unit-based devices replace the traditional manual unit dose cart filling and delivery system and provide increased control over floor stock. Advantages of such systems include smaller size and lower cost relative to centrally-located devices, immediate access to medications, and automated documentation of medication administration.

Point-of-care systems are designed to enable immediate exchange of patient data at the bedside. Such systems allow for rapid access to patient information, fast documentation, integration of hospital information systems, and immediate verification of drug administration. Many systems have been proposed and are described in the literature in all three of the above areas for minimizing or eliminating the above-described disadvantages of the existing systems. Examples of such recent developments are described in U.S. Pat. Nos. 6,032,155; 6,021,392; 5,912,818; 5,314,243; 5,564,803; 6,003,006; 6,068,156; 5,842,976; 5,797,515; 5,014,875; 5,460,294; and 5,713,485.

However, there is still a very pressing need to provide a medication dispensing system which meets the following goals: (1) secure and reliable medication dispensing; (2) more efficient and faster dispensing in comparison to the existing methods; (3) collection of vital signs (i.e., temperature, pulse rate and blood pressure) simultaneously with medication dispensing; (4) maximum automation and employment of computerized paperless operation; (5) automatic management of drug inventory in each department; (6) protection of "drug abuse" by medical and para-medical personnel; and (7) special protection for narcotic drugs.

An object of the present invention is to provide a medication dispensing system, and also a medicine cabinet structure and a tray structure, enabling attaining one or more of the foregoing goals.

BRIEF SUMMARY OF THE PRESENT INVENTION

According to one broad aspect of the present invention, there is provided a medication dispensing system, comprising: a medicine cabinet having a plurality of compartments for containing supplies of different kinds of medications to be accessed by a healthcare attendant for preparing individual medication dosages for named patients; and at least one tray having a plurality of sections for receiving a plurality of receptacles each adapted to contain one or more medication dosages prescribed for a named patient; the medicine cabinet including a cabinet processor having a memory for storing the names of patients and their prescribed medication dosages, and a display screen for displaying the patient names and their respective prescribed medication dosages; the tray including a display screen for displaying the patient names and their respective medication dosages, and a communication link with the medicine cabinet through which the cabinet processor communicates to the tray the patient names and their respective medication dosages.

According to another aspect of the present invention, there is provided a medication dispensing system, comprising: a medicine cabinet having a plurality of compartments for containing supplies of different kinds of medications to be accessed by a healthcare attendant for preparing individual medication dosages for named patients; at least one tray having a plurality of sections for receiving a plurality of receptacles each adapted to contain one or more medication dosages prescribed for a named patient; and a central processor having a memory for storing the patients names and prescribed medication dosages; the medicine cabinet including a communication link with the central processor, and a memory for storing the names of the patients and their prescribed medication dosages communicated thereto by the central processor; the tray including a communication link with the cabinet processor, and having a display for displaying the patient names and their respective medication dosages communicated thereto by the cabinet processor.

According to a further aspect of the present invention, there is provided a medication dispensing system, comprising: a medicine cabinet having a plurality of compartments for containing supplies of different kinds of medications to be accessed by a healthcare attendant for preparing individual medication dosages for named patients; at least one tray having a plurality of sections for receiving a plurality of receptacles each adapted to contain one or more medication dosages prescribed for a named patient; and a central processor having a memory for storing the patients names and prescribed medication dosages; the medicine cabinet including a cabinet processor having a communication link with the central processor, and a plurality of indicators, one for each of the compartments, to indicate the compartment containing the medication supply to be included in a prescribed medication dosage for a named patient.

According to a still further aspect of the present invention, there is provided a medication dispensing system, comprising a medicine cabinet having a plurality of compartments for containing supplies of different kinds of medications to be accessed by a healthcare attendant for preparing individual medication dosages for named patients; at least one tray having a plurality of sections for receiving a plurality of receptacles each adapted to contain one or more medication dosages prescribed for a named patient; and a central processor having a memory for storing the patients names and prescribed medication dosages; the compartments in the medicine cabinet being in the form of drawers which are normally locked but which are selectively unlocked by the cabinet processor when containing a medication supply to be included in a prescribed medication dosage for a named patient; the medicine cabinet further including a plurality of light indicators, one for each of the compartments, controlled by the cabinet processor to indicate the compartment containing the medication supply to be included in a prescribed medication dosage for a named patient.

As used herein in the specification and in the claims section that follows, the term "drawer" includes any type of storage compartment, such as, but not limited to, conventional drawers and bins.

According to yet another aspect of the present invention, there is provided a tray for a medication dispensing system, the tray comprising: a plurality of sections for receiving a plurality of receptacles each adapted to contain one or more medication dosages prescribed for a named patient; and a display screen for displaying the patient names and their respective medication dosages.

According to a still further aspect of the present invention, there is provided a medicine cabinet for a medication dispensing system, the medicine cabinet comprising: a housing including a plurality of compartments for containing supplies of different kinds of medications to be accessed by a health care attendant for preparing individual medication dosages for named patients; a processor having a memory for storing the names of patients and their prescribed medication dosages; and a display screen for displaying the patient names and their respective prescribed medication dosages.

As will be described more particularly below, the above features of the invention, particularly when used together, integrate concepts of point-of-care systems with patient care unit devices, eliminate unnecessary and costly elements, and thus enable an efficient safe system to be attained having a user friendly operation, modular interfacing, computerized tracking and verification at all levels.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

Further features and advantages of the invention will be apparent from the description below.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF A PREFERRED EMBODIMENT

The Overall System

The medication dispensing system described herein closely follows the existing manual decentralized systems, including ward cabinets for the supplies of the various medications, receptacles for the delivery of the medications to individual patients, and trays for delivering the receptacles to the patients. However, the described system enables attaining a higher degree of safety, as well as increased efficiency in the dispensing, replenishing and record-keeping operations. The described system is simple, yet reliable, utilizes relatively basic hardware which can be easily installed and maintained, and requires a minimum of re-training on the part of the nurses or other healthcare attendants.

Figure 1:
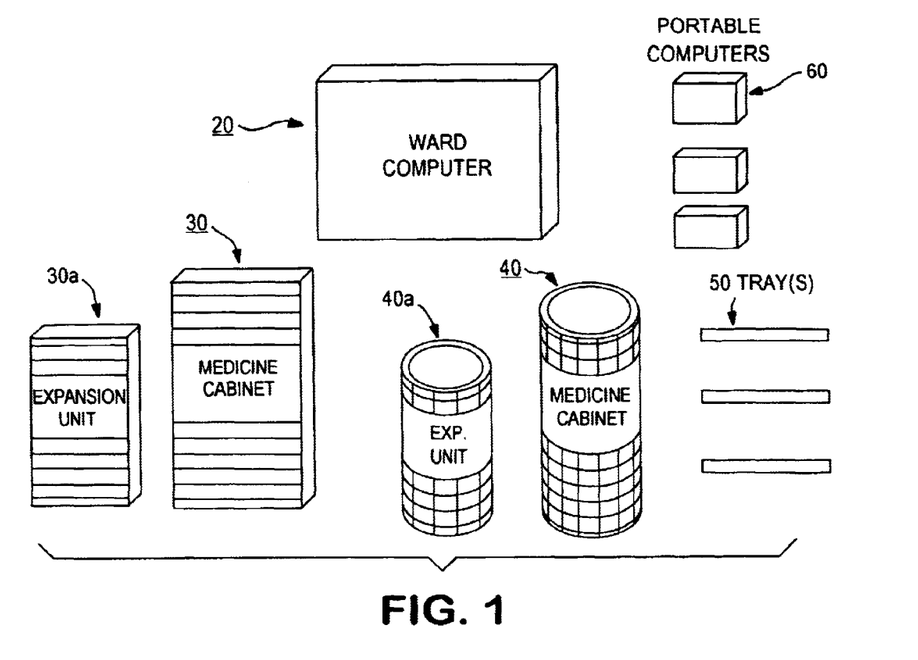
FIG. 1 is a block diagram illustrating the various components of one form of medication dispensing system constructed in accordance with the present invention.

FIG. 1 is a block diagram illustrating the main components of a medication dispensing system constructed in accordance with the present invention as may be provided in a medical institution having a plurality of wards. The illustrated system includes a central (ward) computer, generally designated 20, for each ward or for a group of wards; one or more medicine cabinets of a rectangular type, generally designated 30, and/or of a cylindrical type, generally designated 40; and one or more smart trays, generally designated 50, each adapted to accommodate a plurality of receptacles, generally designated 51, one for each patient in the respective ward. Preferably, each such receptacle is supplemented with an individual locking device. The system illustrated in FIG. 1 further includes a plurality of hand-held, portable computers, each generally designated 60, for use by physicians and/or pharmacists, when writing and/or authorizing prescriptions for individual patients.

As will be described more particularly below, the central computer 20, and each medicine cabinet 30 or 40, include a processor having a memory for storing the names of patients and their prescribed medication dosages, a display screen for displaying the patient names and their respective medication dosages, and a communication link enabling communication between the central computer and the medicine cabinet. Each tray 50 also includes a display screen for displaying the patient names and their respective medication dosages, and a communication link with the medicine cabinet through which the cabinet processor communicates to the tray display screen the patient names and their respective dosages.

As will be described more particularly below, the central processor, the medicine cabinet processor, and the tray enable all the information involved in the dispensing, replenishing and record-keeping operations to be performed electronically without any need for access to patient's written files. Such a system therefore minimizes the possibility of error, and also relieves the nurses or other healthcare attendants of many tasks required in the conventional medication dispensing system. In addition, the described system enables the healthcare attendants to enter vital signs of the patient into the records in order to provide up-dated information of the patient's medical condition.

The Central (Ward) Computer

Figure 2:
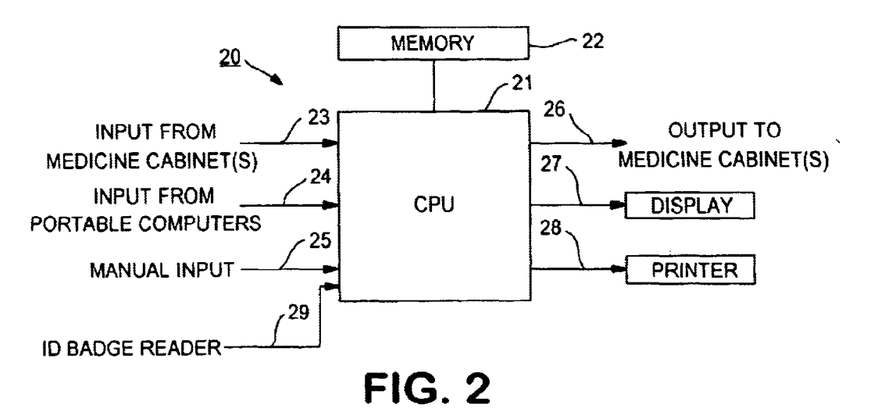
FIG. 2 is a block diagram illustrating the central (or ward) computer in the system of FIG. 1.

FIG. 2 is a block diagram illustrating the main components of the central computer provided in each ward or group of wards. Such a computer includes a conventional CPU (central processor unit) 21 having a memory 22; an input 23 from the medicine cabinet(s) (30, 40, FIG. 1); an input 24 from the portable units (60, FIG. 1); an input 29 from the I.D. badge reader; and one or more manual inputs 25, such as a keyboard, touch screen, mouse, and the like. The central processor 21 includes an output 26 to the medicine cabinet(s) 30, 40; a display 27; and a printer 28, e.g., for printing inventory records, management reports, etc. The central ward computer 20 does not have (but may have) a direct output to the trays 50 since it communicates with those trays via the medicine cabinet(s) 30, 40 as will be described below.

A main task of the ward computer 20 is to manage (open, update and remove) all patient entries in the respective ward, with every entry containing the following information for the respective patient: name; identification as appearing on a bar code printed on the wristband to be worn by the patient; referring and treating physicians; relatives; allergies; medication orders, including an electronic signature by both the physician and the authorizing pharmacist; the vital signs of the respective patient as collected and stored during physician rounds and/or medication dispensing rounds; and information about all medications received by the patient while in the respective ward. The patient entry also includes a flag indicating if the respective entry is active or deactivated (e.g., by the release or transfer of the patient to another ward).

The ward computer 20 also serves as a simple and friendly man-machine interface for the entry of the physician's orders regarding medications. Such entries may be done by manually inputting this information, or by automatically inputting the information via the portable units 60. At the end of each physician's order entry, the entry must be validated by an electronic signature of the physician, e.g., via the portable unit 60, or by a reader 29 reading the personal identification badge of the treating physician.

The ward computer 20 also serves as a simple and friendly man-machine interface in the dispensing of the medications to the patient from the medicine cabinet(s) 30, 40, and in the replenishing of the medicine cabinets. All operations of the medicine cabinet(s) are documented in the computer's memory 22 and may be printed out or displayed at any desired time in the form of reports. Each such operation requires the person initiating the operation to be identified by name or employee number, followed by the personal code or identification badge, e.g., as read by the I.D. badge reader 29.

The ward computer 20 also maintains a running inventory of the contents of each medicine cabinet 30, 40, including a list of the different kinds of medications and their locations in the matrix of drawers in the respective cabinet. Such inventories are continuously updated as the medications are dispensed and as the supplies are replenished. This task also allows for the addition of a new medication to be dispensed, or the removal of a medication no longer required to be dispensed.

The ward computer 20 may also produce a wide variety of reports and records, including: current inventories in each ward cabinet; the replenishing level of each medication; information concerning patient files, individually and collectively; information concerning patient vital signs, e.g., for graphic display; information regarding all dispensing and replenishing of medications from the medicine cabinets, including date, time, names, etc.; replenishing forms to be directed to the pharmacy for replenishing a medication (a task which can also be performed by linking to the pharmacy computer); forms for emergency medication; and summaries of all the medications received by a particular patient during the stay in the respective ward, including billing, etc.

As indicated above, the ward computer 20 communicates directly with the medicine cabinet(s) (30, 40) regarding the inventory of medications and their locations in the cabinet, the names of the patients and their prescribed medication dosages; the type and quantities of medications as dispensed and as replenished; and the vital signs data with respect to the patients as inputted manually, via the tray 50, or via the portable units 60, during an examination by the physician or the dispensing of a medication to the patient.

Figure 3:
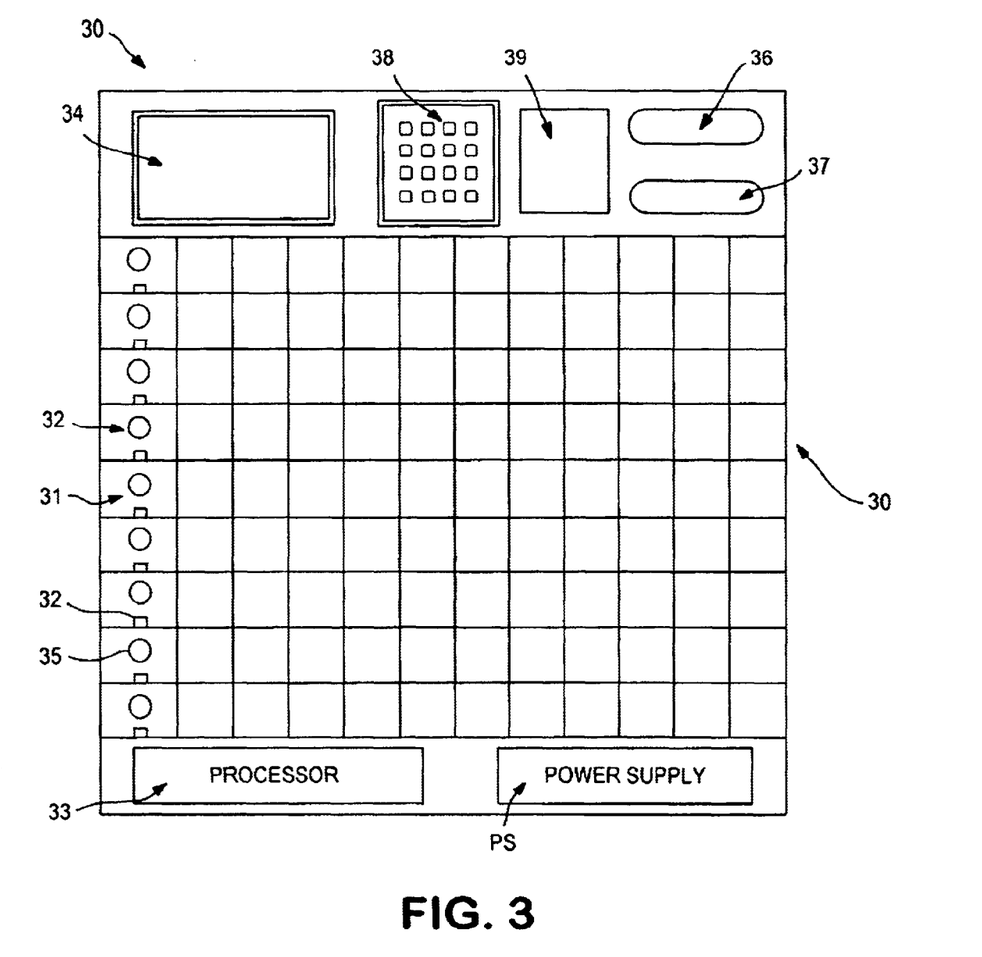
FIG. 3 is a diagram more particularly illustrating one form of medicine cabinet in the system of FIG. 1.
Figure 4:
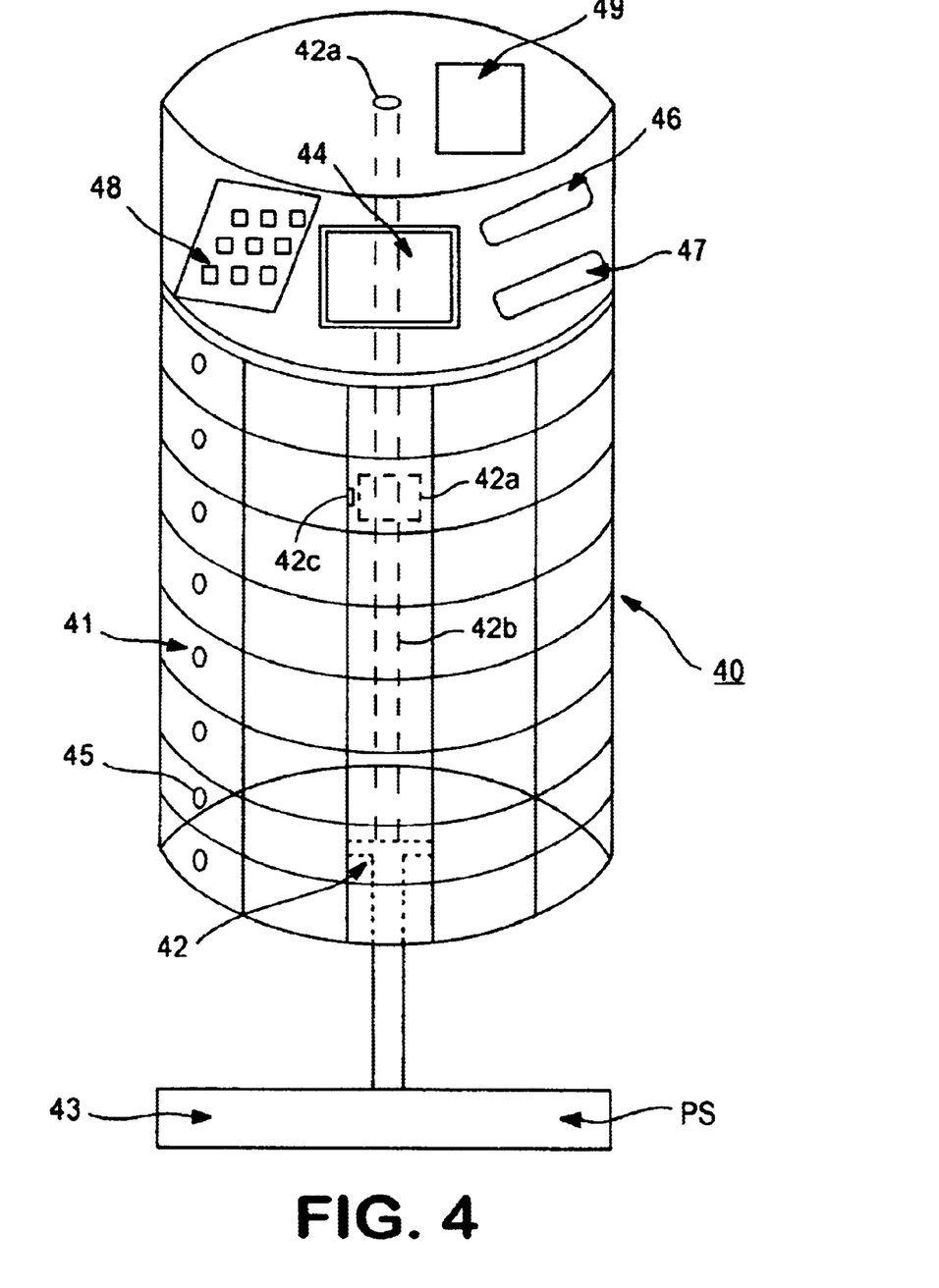
FIG. 4 is a block diagram more particularly illustrating a second form of medicine cabinet in the system of FIG. 1.

The Construction of the Medicine Cabinet (FIGS. 3 and 4)

As indicated earlier, each ward may be provided with one or more medicine cabinets of the rectangular type 30 and/or of the cylindrical type 40. FIG. 3 diagrammatically illustrates the construction of a rectangular medicine cabinet 30; whereas FIG. 4 illustrates the construction of a cylindrical medicine cabinet 40. In both cases, the medicine cabinet has a plurality of compartments for containing supplies of the different kinds of medications to be accessed by a healthcare attendant for preparing individual dosages to be delivered to the respective patients via the trays 50 and receptacles 51. The medicine cabinet further acts as a communication link between the trays 50 and the ward computer 20 for recording in the ward computer vital signs of the respective patients as may be taken during the dispensing of the medications to them.

The medicine cabinet 30 shown in FIG. 3 includes a rectangular housing in which the medication compartments are in the form of drawers 31 arranged in a rectangular array, consisting of a plurality of horizontal rows and vertical columns. Each drawer 31 preferably includes a lock, shown schematically at 32, which normally locks the drawer in its closed position, but which is selectively actuatable to release the drawer to enable it to be pulled out by the healthcare attendant in order to access the medication supply within the drawer.

The illustrated medicine cabinet further includes a processor 33 having a memory for storing the names of patients and the prescribed medication dosages as communicated thereto via the ward computer 20. The medicine cabinet further includes a screen 34 for displaying this information, and a plurality of light indicators 35, one for each drawer 31, selectively energized, preferably with a flashing light, to indicate the compartment containing the medication to be dispensed to a named patient.

The medicine cabinet 30 further includes a communication link 36 with the ward computer 20, and another communication link 37 with the trays 50. Such communication links are schematically shown as connectors for wired communication, but could also be transmitters and receivers (e.g., RF, IR, acoustical) for wireless communication. A keyboard 38 serves for manually inputting data, besides the data inputted via the communication links 36, 37. The display screen 34 may also be a touch screen for inputting data.

The illustrated medicine cabinet 30 further includes a label printer 39. As will be described below, such a printer may also be used for printing labels to be applied to the drawers 31 to identify the medications contained therein, particularly as new medications are added. Printer 39 may also be used, if necessary, for printing the wristbands and bar codes to be applied to the patients for identifying them.

The foregoing components of the medicine cabinet 30 illustrated in FIG. 3 are powered by a power supply, indicated by box PS, which preferably also includes a back-up unit in the event of power failure.

Such a cabinet has a capability of accommodating a large number of different medications. If needed, a ward may be provided with more than one such cabinet, or the capacity of such a cabinet may be increased by having one or more expansion units, shown schematically at 30a in FIG. 1. Such an expansion unit would provide additional drawers 31a but would include a cable connection to he master medicine cabinet 30 in order to enable the expansion unit to share its processor, and possibly also its display screen.

Medicine cabinet 40, as particularly illustrated in FIG. 4, is capable of accommodating a larger number of medications. Such a cabinet includes a cylindrical housing having a plurality of medication drawers 41 that are arranged according to a matrix of horizontal circular rows and vertical columns.

The illustrated medicine cabinet 40 further includes a rotary drive, schematically indicated at 42, for rotating the cylindrical array of drawers, and a selector member, schematically shown at 42a, driven vertically along a central rod 42b, for selecting one of the drawers to be accessed. This may be done, for example, by having the selector member 42a release a spring lock, shown schematically at 42c, for the selected drawer enabling a spring (not shown) to project the selected drawer forwardly out of the array. Such a selected drawer may be returned to its normal, locked position by manually pushing it back into the array, whereupon its spring lock 42c would be engaged to lock it in position.

Medicine cabinet 40 illustrated in FIG. 4 also includes a processor 43 having a memory for storing the names of patients and their respective medication dosages, and a display screen 44 for displaying such information. Each drawer 41 may also be provided with a light indicator 45 controlled by the processor 43 to indicate the drawer containing the medication to be accessed for a particular patient, although an indicator 45 is not essential in this case since the selected drawer is automatically unlocked and projected forwardly by the selector unit 42a as described above.

Medicine cabinet 40 illustrated in FIG. 4 further includes a communication link 46 with the ward computer 20, a communication link 47 with the tray 50, a manual-input keyboard 48, a label printer 49, and power supply PS, corresponding to the comparable elements in medicine cabinet 30 as described above with respect to FIG. 3.

As shown in FIG. 1, the capacity of medicine cabinet 40 may also be expanded by adding one or more expansion units, shown at 40a in FIG. 1. Such an expansion unit would also be a cable-connected to the medicine cabinet 40 to enable the expansion unit also to share its processor, as well as the display screen or other components if desired.

For example, a separate expansion unit 40a for medicine cabinet 40 (or expansion unit 30a for medicine cabinet 30) may be provided for special medications, e.g., those requiring cooling storage, and/or special protective measures to control access. Where cooling is required, the cabinet expansion unit would include a refrigeration unit, similar to a mini-bar refrigerator; and where special security measures are required, the cabinet expansion unit could be normally locked and unlocked only when a proper and valid password or personal identification is inputted.

The Construction of the Trays 50

Figure 5:
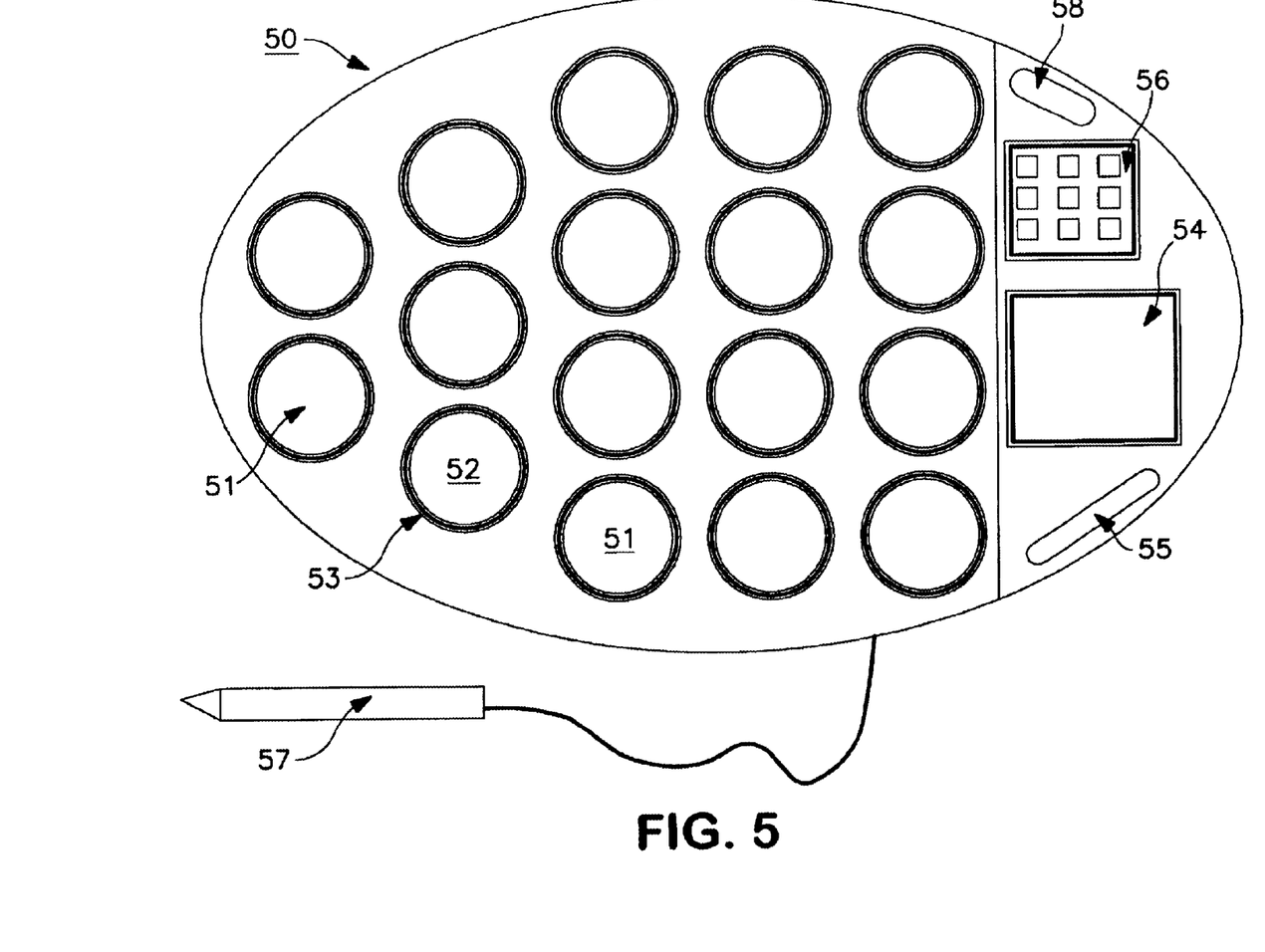
FIG. 5 is a diagram illustrating the construction of the tray in the system of FIG. 1.

FIG. 5 diagrammatically illustrates the construction of each of the trays 50. As indicated above, each of the trays 50 is adapted to carry a plurality of receptacles, such as plastic cups and shown at 51 in FIG. 1, for the patients in the respective ward, there being one (or more) such receptacles for receiving the medication dosages of each patient. The tray 50 would normally be supported on a shelf to the side of the medicine cabinet (30, 40), or on wheeled equipment normally used for taking vital signs of the patient.

Each tray 50 includes a plurality of sections, in the form of depressions or wells 52, for receiving the various containers 51. Preferably, each well 52 is circumscribed by an indicator light 53 which is energized, preferably with a flashing light, to indicate the receptacle for the respective patient.

Each tray 50 further includes a display screen 54 for displaying the patient names and their respective medication dosages. The tray further includes a processor having a memory and a communication link 55, e.g., wired or wireless, with the processor (33 or 43) of the respective medicine cabinet 30, 40, to enable the latter processor also to control the light indicators 53 and the display screen 54 of the tray. Each tray 50 further includes a keyboard 56 for manually entering data, and a bar code reader 57 for reading the bar code on a patient's wrist, to enable matching that patient with the patients name displayed on the display screen 54.

Tray 50 illustrated in FIG. 5 also enables the nurse or other healthcare attendant to enter vital signs information concerning the respective patient at the time medication is dispensed to the patient. Such vital signs data may include temperature, blood pressure, pulse rate, and any other information that may be relevant to the health status of the patient and the possible need to change the medication. For this purpose, tray 50 includes a communication link 58, e.g., wired or wireless, to the examination equipment for automatically transferring the data therefrom via communication link 55 to the medicine cabinet, where the data is stored and transferred at the appropriate time to the central ward computer 20. Such data may also be manually entered via the keyboard 56.

The Construction of the Hand-Held Computer 60

Figure 6:
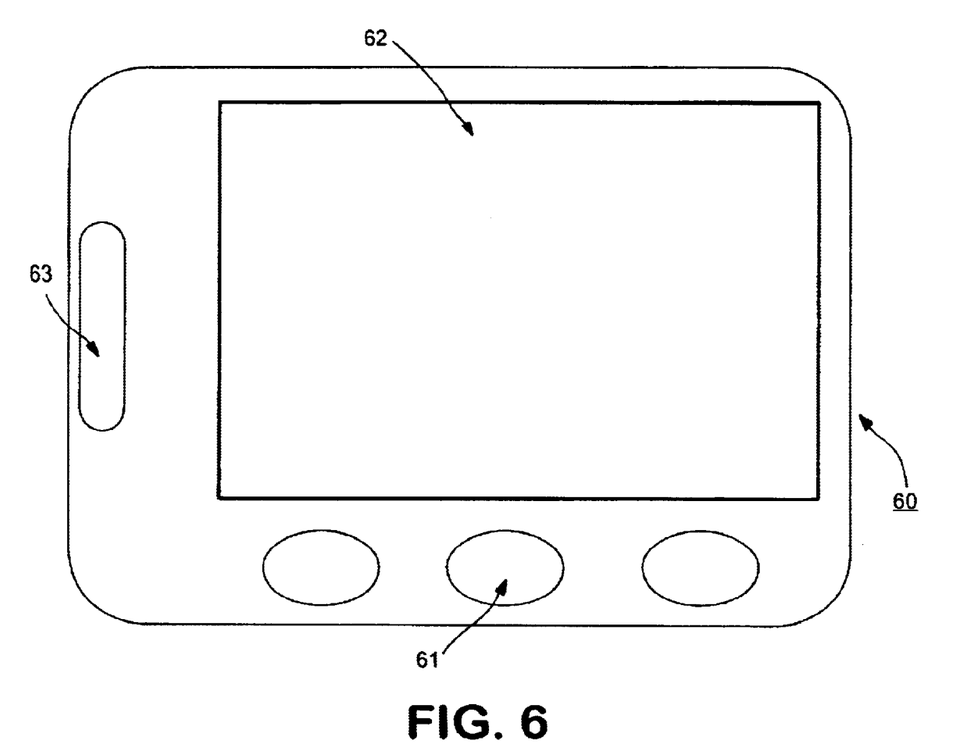
FIG. 6 is a diagram more particularly illustrating the portable computer for the physician and/or pharmacist in the system of FIG. 1.

Every system for the safe and efficient dispensing of medication requires a computerized patient file containing at least the details of the patient and the medication the patient is to receive. This data may be hand-entered in the central ward computer 20 from hand-written notes, e.g., prepared at the time of the physician rounds. However, a far better alternative is to use a hand-held computer 60 as illustrated in FIG. 6.

Computer 60 includes a keyboard 61 containing data-entry and functional keys; a large display 62, preferably of the touch screen type to enable inputting information in this manner; and a communication link 63, which may be wired or wireless, to establish communication with the ward computer 20.

Such a hand-held computer allows the physician to prescribe certain medications, or to change them or their dosages, while making the rounds. The hand-held computer also receives and retains the physician's, and/or the pharmacist's electronic signature, together with the rest of the data collected. At the end of the rounds, the hand-held computer 60 may be coupled to the ward computer 20 so as to transfer thereto all the data collected in the hand-held computer, including the electronic signature of the physician and/or pharmacist. This information, including electronic signatures, is entered into the records of the respective patients as maintained by the memory within the ward computer 20. The hand-held computer may also be used for entering data into the ward computer, or for displaying on the hand-held computer or the ward computer, the vital signs and any other pertinent data taken by the physician during the respective round.

OPERATION

The described medication dispensing system may be used in performing a number of process as follows:

Initial Data Entry

When a patient enters the respective ward, a patient file is opened by entering the patient's name, code (preferably also printed on a wristband as a bar code), referring physician and treating physician, relatives, allergies, medication orders including any required electronic signatures by the physician and/or pharmacist, and any other relevant data needed. As indicated earlier, this information is entered manually, and/or by the portable hand-held computer 60.

Preparing Dosages

When medication dispensing time has arrived, or when dispensing of medication is otherwise needed, the healthcare attendant first has to identify himself or herself to the ward computer, and then enter a code or use a personal identification means to a reading device proximate to the computer. Only when the correct identification process is completed, the ward computer 20 enables the medicine cabinet to be accessed by the attendant.

If the medicine cabinet (30, 40) is available, the ward computer 20 downloads the list of patients to receive medication at that time, identifying each patient, the medication, and the dosage for the respective patient. This information is communicated via computer port 26 and the cabinet communication link (36, 46) and is displayed per patient on the display screen (34, 44) of the medicine cabinet.

For each patient's name displayed, also displayed is the prescribed medication dosage, and the appropriate drawer for the respective medication is indicated (by indicator lights 32, 45) and unlocked to provide access to the medication in the drawer, and/or pushed forward with cabinet 40.

If the prescribed medication is not available in the medicine cabinet, the medicine cabinet guides the nurse via its display to order the medication from the central pharmacy; at the same time, the ward computer issues an order form for the central pharmacy, or otherwise orders the appropriate medication through its communication with the central pharmacy.

The attendant then checks if the name of the medication displayed on the screen 44,34 matches that on the drawer identified by the flashing light (35, FIG. 3) or unlocked and projecting forwardly (FIG. 4). Assuming there is a match, the attendant withdraws the medication package from the drawer and verifies that the medicine within the noted drawer is the stated medication, removes the dosage specified on the screen, places the dosage in the receptacle 51 for the respective patient, returns the medication package to its drawer, closes the drawer, and optionally makes an entry of the dosage removed via the keyboard 38,48.

When the cabinet senses that the drawer has been closed, the processor repeats the foregoing cycle with respect to the next medication to be dispensed to the respective patient, and the attendant places the removed dosage in the same receptacle 51 for the respective patient. This continues until all the specified medications for the respective patient have been removed and placed into the patient's receptacle, this receptacle is now placed in the flashing well on the surface of tray 50. The tray stores in its memory the exact location of the said receptacle which will be retrieved later at the point of care for the respective patient.

The system then repeats the foregoing operations with respect to all the other patient's on the list, with the medications for each patient being placed in a separate receptacle for the respective patient, and with each receptacle being placed in a separate well 52 of the tray 50. Each separate receptacle is identified by a label printed by the label printer (39, 49) of the medicine cabinet.

Delivery of Medications to the Patients

The tray 50, carrying the individual receptacles 51 for each patient, with each receptacle optionally covered and including all the medications to be taken by the respective patient, is then taken to the patients in the ward for delivery of each receptacle to the respective patients. For this purpose, the tray 50 may be placed on a trolley with the medical equipment for the collection of vital signs. The attendant delivers the medications to the patients in the following manner for each patient:

When the attendant arrives with the tray at the patient's bedside, the attendant uses the bar code reader 57 to scan the patient's wristband.

This causes the light indicator 53 for the respective receptacle 51 to be energized, preferably by flashing light. The patient's name is also displayed on the screen 54 together with the list of medications in the respective receptacle 51, the total number of medications in the receptacle, and the list of vital signs to be obtained by the attendant. If a prescribed medication had not been available from the medicine cabinet and therefore had been ordered directly from the central pharmacy as described above, the tray display 54 would include a reminder of this fact to the attendant.

The attendant then removes the receptacle from the indicated well 52 on the tray, matches the printed name on the label with the display on the tray, counts the total number of medications in the receptacle, and matches the total number with the total number in the display. Assuming a match occurs in all these respects, the attendant then hands the patient the respective receptacle 51 of medications.

If certain vital signs are to be taken of the patient at this time (e.g., temperature, blood pressure, pulse rate, etc.) as instructed via the tray display screen 54, the attendant attends to this and inputs this information via the tray connector 58 or manually via the keyboard 56. This information is collected and stored in a storage device provided in the tray 50 until the end of the round. At that time, such information for all the patients is communicated via connector 57 to the medicine cabinet (30, 40), and via its connector to the ward computer 20. The vital signs information may be collected before, during, or after the dispensing of the medications, and validated for the respective patient by the bar code reader 57.

Replenishing the Medicine Cabinet

This procedure is under the full surveillance and guidance of the medicine cabinet processor and the ward computer. Whenever the medicine cabinet indicates a "low level" of medication in one of the drawers, this fact is displayed on the medicine cabinet screen (34, 44), and the display thereon requests the attendant to reorder the identified medication from the central pharmacy via forms, or via a special communication channel between the pharmacy computer and the ward computer.

The ward computer 20 may be requested at any time to authorize a replenishment from the central pharmacy. If the ordering is done with forms (i.e., without direct communication), the ward computer should be supplied with a list of medications received from the pharmacy, including the exact amount of every new medication. The ward computer updates the inventory and transmits the updated inventory to the medicine cabinet. For each such medication, the medicine cabinet processor performs the following operations:

1. The cabinet processor (33, 43) displays the name of the medication on the respective cabinet screen, and concurrently indicates, and/or unlocks, the corresponding drawer of the medicine cabinet. If the medication is a new one that was not previously provided in the medicine cabinet, the cabinet opens an empty drawer that was not in use, has its label printer print a label identifying the new medication, and instructs the attendant, via the display screen, to apply the label to the front of the drawer. If any particular medication is needed in relatively large quantities, a plurality of drawers may be allocated to the respective medication.

2. The attendant then opens the packaging of the medication and places the medication in the open drawer. At this time, the attendant again must match the name on the package with the name on the front of the open drawer; for further safety, the attendant may be required to scan the bar code on the medication packaging to match it with the name of the medication displayed on the screen.

3. The attendant then closes the . When the closed drawer is sensed by the medicine cabinet, its processor repeats the foregoing cycle for all the remaining medications on the list for replenishment. If during such a replenishing operation the attendant notes that one of the drawers is full, the attendant may press a "full" button on the cabinet keyboard (or on the display screen, if a touch screen is used), whereupon the cabinet processor will open an empty drawer print a label with the name of the medication, and instruct the attendant to stick it on the new open drawer.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A medication dispensing system, comprising:
   a medicine cabinet having a plurality of drawers for containing supplies of different kinds of medications to be accessed by a healthcare attendant for preparing individual mediation dosages for named patients;

and at least one tray having a plurality of sections for receiving a plurality of receptacles each adapted to contain one or more medication dosages prescribed for a named patient;

said medicine cabinet including a cabinet processor having a memory for storing the names of patients and their prescribed medication dosages, a display screen for displaying said patient names and their respective prescribed medication dosages, and an expansion cabinet including an additional plurality of drawers for containing additional supplies of medications, a communication link with said cabinet processor for selectively controlling said additional plurality of drawers, and a plurality of light indicators, one for each of said additional drawers controlled by said processor;

said tray including a display screen for displaying the patient names and their respective medication dosages, and a communication link with said medicine cabinet through which said cabinet processor communicates to said tray the the patient names and their respective medication dosages.

2. The system according to claim 1, wherein said drawers in the medicine cabinet are normally locked but which are selectively unlocked by said cabinet processor when containing a medication supply to be included in a prescribed medication dosage for a named patient.

3. The system according to claim 1, wherein said medicine cabinet further includes a plurality of light indicators, one for each of said drawers controlled by said cabinet processor, to indicate the compartment containing the medication supply to be included in a prescribed medication dosage for a named patient.

4. The system according to claim 1, wherein said tray further includes a reader device for reading an identification of a named patient to enable matching the read identification with an identification communicated by said medicine cabinet of a named patient to receive a prescribed medication dosage.

5. The system according to claim 4, wherein said reading device is a bar code reader to read the bar code on a wrist band carried by the respective patient.

6. The system according to claim 1, wherein said tray further includes a light indicator for each of said sections selectively energizable to indicate the section to receive the receptacle of a prescribed medication dosage for a named patient.

7. The system according to claim 6, wherein said tray sections are circular wells in the tray, and said light indictors are of annular configuration circumscribing their respective wells.

8. The system according to claim 1, wherein said medicine cabinet further includes a label printer for printing the names of new medications to be introduced into empty drawers to receive supplies of the new medications.

9. The system according to claim 1, wherein said cabinet processor further stores in its memory a running inventory of each medication supply in each drawers including all quantities supplied less all dosages removed.

10. The system according to claim 1, wherein the system further comprises a central processor having a memory for storing said patient names and the respective medication dosages prescribed for said patients; and a communication link with said medicine cabinet through which said central processor communicates to said cabinet processor the patient names and their respective prescribe medication dosages.

11. The system according to claim 10, wherein one of said processors stores in its memory running inventories of the medications in said drawers including all quantities introduced into the respective drawer less all dosages removed therefrom.

12. The system according to claim 10, wherein said tray includes an input device for inputting data regarding vital signs of a respective patients, and said communication link of the tray with the cabinet processor communicates said vital signs data to said central processor via said cabinet processor and its communication link with the central processor.

13. The system according to claim 10, wherein the system further comprises a plurality of portable computer units for use by physicians and/or pharmacists; each of said portable computer units including an input device for inputting data regarding a prescribed medication dosage for a named patient, a storage device for storing the electronic signature of the user, and a communication link for communicating to said central processor said inputted data and said electronic signature.

14. A medicine cabinet for a medication dispensing system, said medicine cabinet comprising:

a housing including a plurality of drawers for containing supplies of different kinds of medications to be accessed by a health care attendant for preparing individual medication dosages for named patients;

a processor having a memory for storing the names of patients and their prescribed medication dosages;

a display screen for displaying said patient names and their respective prescribed medication dosages; and and an expansion cabinet including an additional plurality of drawers for containing additional supplies of medications, a communication link with said cabinet processor for selectively controlling said additional plurality of drawers, and a plurality of light indicators, one for each of said additional drawers controlled by said processor.

15. The medicine cabinet according to claim 14, wherein said medicine cabinet further includes a plurality of light indicators, one for each of said drawers controlled by said processor, to indicate the drawer containing the medication supply to be included in a prescribed medication dosage for a named patient.

16. The medicine cabinet according to claim 15, wherein said drawers are normally locked but which are selectively unlocked by said processor when containing a medication supply to be included in a prescribed medication dosage for a named patient.

17. The medicine cabinet according to claim 16, wherein said housing is of rectangular configuration, and said drawers are arranged therein according to a rectangular matrix of a plurality of horizontal rows and vertical columns.

18. The medicine cabinet according to claim 16, wherein said housing is of cylindrical configuration, and said drawers are arranged therein according to a cylindrical matrix of a plurality of horizontal circular rows and vertical columns.

19. The medicine cabinet according to claim 18, wherein said medicine cabinet further includes a selector movable within said cylindrical matrix along a circular horizontal path, and also along a linear vertical path, to selectively enable said drawers for removing a medication supply therefrom and for replenishing the medication supply therein.

20. The medicine cabinet according to claim 14, wherein said medicine cabinet further includes a label printer for printing the names of new medications to be applied to empty drawers to receive supplies of the new medications.

21. The medicine cabinet according to claim 14, wherein said processor further stores in its memory a running inventory of each medication supply in each drawer including all quantities supplied less all dosages removed.

* * * * *